US011510742B2

(12) United States Patent
Eil

(10) Patent No.: US 11,510,742 B2
(45) Date of Patent: Nov. 29, 2022

(54) SYSTEM AND METHOD OF UTILIZING COMPUTER-AIDED IDENTIFICATION WITH MEDICAL PROCEDURES

(71) Applicant: Alcon Inc., Fribourg (CH)

(72) Inventor: Martin Eil, Berlin (DE)

(73) Assignee: Alcon Inc., Fribourg (CH)

( * ) Notice: Subject to any disclaimer, the term of this patent is extended or adjusted under 35 U.S.C. 154(b) by 264 days.

(21) Appl. No.: 16/813,304

(22) Filed: Mar. 9, 2020

(65) Prior Publication Data

US 2020/0305987 A1 Oct. 1, 2020

Related U.S. Application Data

(60) Provisional application No. 62/823,938, filed on Mar. 26, 2019.

(51) Int. Cl.

| | |
|---|---|
| ***A61B 34/00*** | (2016.01) |
| ***A61B 90/20*** | (2016.01) |
| ***G16H 10/65*** | (2018.01) |
| ***A61B 5/1171*** | (2016.01) |
| ***G06V 40/16*** | (2022.01) |

(52) U.S. Cl.

CPC ............ *A61B 34/25* (2016.02); *A61B 5/1176* (2013.01); *A61B 90/20* (2016.02); *G06V 40/165* (2022.01); *G06V 40/172* (2022.01); *G16H 10/65* (2018.01); *A61B 2034/254* (2016.02); *A61B 2034/256* (2016.02); *A61B 2034/258* (2016.02); *G06V 2201/034* (2022.01)

(58) Field of Classification Search

CPC ....... A61B 90/20; A61B 34/25; A61B 5/1176; A61B 2034/254; A61B 2034/258; A61B 2034/256; G06V 40/165; G06V 40/172; G06V 2201/03; G06V 40/179; G06V 2201/034; G16H 10/65

See application file for complete search history.

(56) References Cited

U.S. PATENT DOCUMENTS

| | | | | |
|---|---|---|---|---|
| 2008/0181465 A1* | 7/2008 | Sauerwein | ............... | G07C 9/37 382/115 |
| 2018/0373925 A1 | 12/2018 | Wang et al. | | |
| 2019/0027239 A1 | 1/2019 | Soto Santos | | |
| 2020/0202154 A1* | 6/2020 | Wang | .................. | G06V 40/172 |

* cited by examiner

*Primary Examiner* — Brenda C Bernardi

(57) ABSTRACT

The disclosure provides a system that may receive an identification of a first patient; may receive a first template that includes first multiple locations associated with a face of the first patient and associated with the identification of the first patient; may determine second multiple locations associated with a face of a current patient; may determine a second template of the face of the current patient based at least on the second multiple locations associated with the face of the current patient; may determine if the first template matches the second template; if the first template matches the second template, may provide an indication that the current patient has been correctly identified as the first patient; and if the first template does not match the second template, may provide an indication that the current patient has not been identified.

10 Claims, 15 Drawing Sheets

300 350 340 330 310 320 420

SYSTEM AND METHOD OF UTILIZING COMPUTER-AIDED IDENTIFICATION WITH MEDICAL PROCEDURES

BACKGROUND

Field of the Disclosure

This disclosure relates to computer-aided identification and more particularly to utilizing computer-aided identification with medical procedures.

Description of the Related Art

In the past, a failure to correctly identify a patient could result in transfusion errors, medication errors, incorrect person procedures, testing errors, and/or wrong medical procedure site errors, among others. Patient misidentification can be a root cause in medical procedure errors. Areas where patient misidentification can occur include surgical interventions, blood transfusions, drug administration, and/or phlebotomy, among others. Patient misidentification can be caused by name structures (e.g., close similarity of names), inaccuracies dates of births, clothing that conceals identity, non-conscious patients, errors when registering patients via computerized systems, an identification wrist band not present, an identification wrist band that identifies another (e.g., incorrect) patient, etc.

SUMMARY

The present disclosure provides a system able to receive an identification of a first patient. In one example, the system may receive the identification of the first patient from medical personnel. In another example, the system may receive the identification of the first patient via scanning a wristband of the patient. The system may further receive a first template that includes first multiple locations associated with a face of the first patient and associated with the identification of the first patient. In one example, the system may receive the first template that includes first multiple locations associated with the face of the first patient and associated with the identification of the first patient from a storage device. In one example, the system may receive the first template that includes first multiple locations associated with the face of the first patient and associated with the identification of the first patient from a network. The system may further determine second multiple locations associated with a face of a current patient. For example, a medical procedure may be pending for the current patient.

The system may further determine a second template of the face of the current patient based at least on the second multiple locations associated with the face of the current patient. For example, a facial recognition system, method, and/or process may determine the second template of the face of the current patient based at least on the second multiple locations associated with the face of the current patient. The system may further determine if the first template matches the second template. For example, the system may determine if the first template matches the second template to confirm or to disaffirm that the current patient is the first patient. If the first template matches the second template, the system may further provide, via a display, an indication that the current patient has been correctly identified as the first patient. If the first template does not match the second template, the system may further provide, via a display, an indication that the current patient has not been identified. For example, providing the indication that the current patient has not been identified may include providing at least one of a visual signal and an audible signal. In determining if the first template matches the second template, the system may determine if a polygon formed by three or more locations of the first multiple locations of the first template matches a polygon formed by three or more locations of the second multiple locations of the second template.

The system may further determine, based at least on the second template, that surgical tooling equipment enters an area of the second template. For example, the area of the second template may be associated with an area of the first patient where the medical procedure may not be performed. The system may further provide an indication that the surgical tooling equipment should not be in the area of the second template. For example, providing the indication that the surgical tooling equipment should not be in the area of the second template may be performed in response to determining, based at least on the second template, that the surgical tooling equipment enters the area of the second template.

The system may further determine the first multiple locations associated with the face of the first patient and may further determine the first template of the face of the first patient based at least on the first multiple locations associated with the face of the first patient. In one example, a facial recognition system, method, and/or process may determine the first multiple locations associated with the face of the first patient. In another example, a facial recognition system, method, and/or process may determine the first template of the face of the first patient based at least on the first multiple locations associated with the face of the first patient. The first template may be determined before a medical procedure. For example, the first template may be utilized to confirm that the first patient is the first patient before a medical procedure begins or proceeds.

The system may further associate the first template with the identification of the first patient and store the first template with the identification of the first patient. In one example, the system may store the first template with the identification of the first patient via a storage device. In another example, the system may store the first template based on the identification of the first patient. Storing the first template based on the identification of the first patient may permit and/or may facilitate utilizing the identification of the first patient to retrieve and/or receive the first template.

The system may further determine an angle of a microscope with respect to the face of the first patient based at least on the second template. For example, determining a position of a surgeon, with respect to the first patient, may be based at least on determining the angle of the microscope with respect to the face of the first patient based at least on the second template. The microscope may be or include a microscope integrated display. The system may further determine an orientation of a lens with respect to the face of the first patient based at least on the second template. For example, the lens may be utilized in the medical procedure. For example, the lens may be placed in an eye of the first patient.

The system may further determine third multiple locations associated with a face of a second patient, determine a third template of the face of the second patient based at least on the third plurality of locations associated with the face of the second patient, associate the third template with an identification of the second patient, and store the third template with the identification of the second patient. For example, the system may be utilized with other patients.

The system may include a microscope integrated display. The microscope integrated display may include at least one image sensor configured to acquire at least one image. In one example, the microscope integrated display may acquire the at least one image. In another example, determining the second multiple locations associated with the face of the current patient may include determining the second multiple locations associated with the face of the current patient via the at least one image acquired via the microscope integrated display.

The present disclosure further includes a non-transient computer-readable memory device with instructions that, when executed by a processor of a system, cause the system to perform the above steps. The present disclosure further includes a system or a non-transient computer-readable memory device as described above with one or more of the following features, which may be used in combination with one another unless clearly mutually exclusive: i) receive an identification of a first patient; ii) receive a first template that includes first multiple locations associated with a face of the first patient and associated with the identification of the first patient; iii) determine second multiple locations associated with a face of a current patient; iv) determine a second template of the face of the current patient based at least on the second multiple locations associated with the face of the current patient; v) determine if the first template matches the second template; vi) if the first template matches the second template, provide an indication that the current patient has been correctly identified as the first patient; vii) if the first template does not match the second template, provide an indication that the current patient has not been identified; viii) determine, based at least on the second template, that surgical tooling equipment enters an area of the second template; ix) in response to determining, based at least on the second template, that the surgical tooling equipment enters the area of the second template, provide an indication that the surgical tooling equipment should not be in the area of the second template; x) determine the first multiple locations associated with the face of the first patient; xi) determine the first template of the face of the first patient based at least on the first multiple locations associated with the face of the first patient; xii) associate the first template with the identification of the first patient; xiii) store the first template with the identification of the first patient; xix) determine an angle of a microscope with respect to the face of the first patient based at least on the second template; xx) determine an orientation of a lens with respect to the face of the first patient based at least on the second template; xxi) determine third multiple locations associated with a face of a second patient; xxii) determine a third template of the face of the second patient based at least on the third multiple locations associated with the face of the second patient; xxii) associate the third template with an identification of the second patient; and xxiv) store the third template with the identification of the second patient.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

Figure 1A:
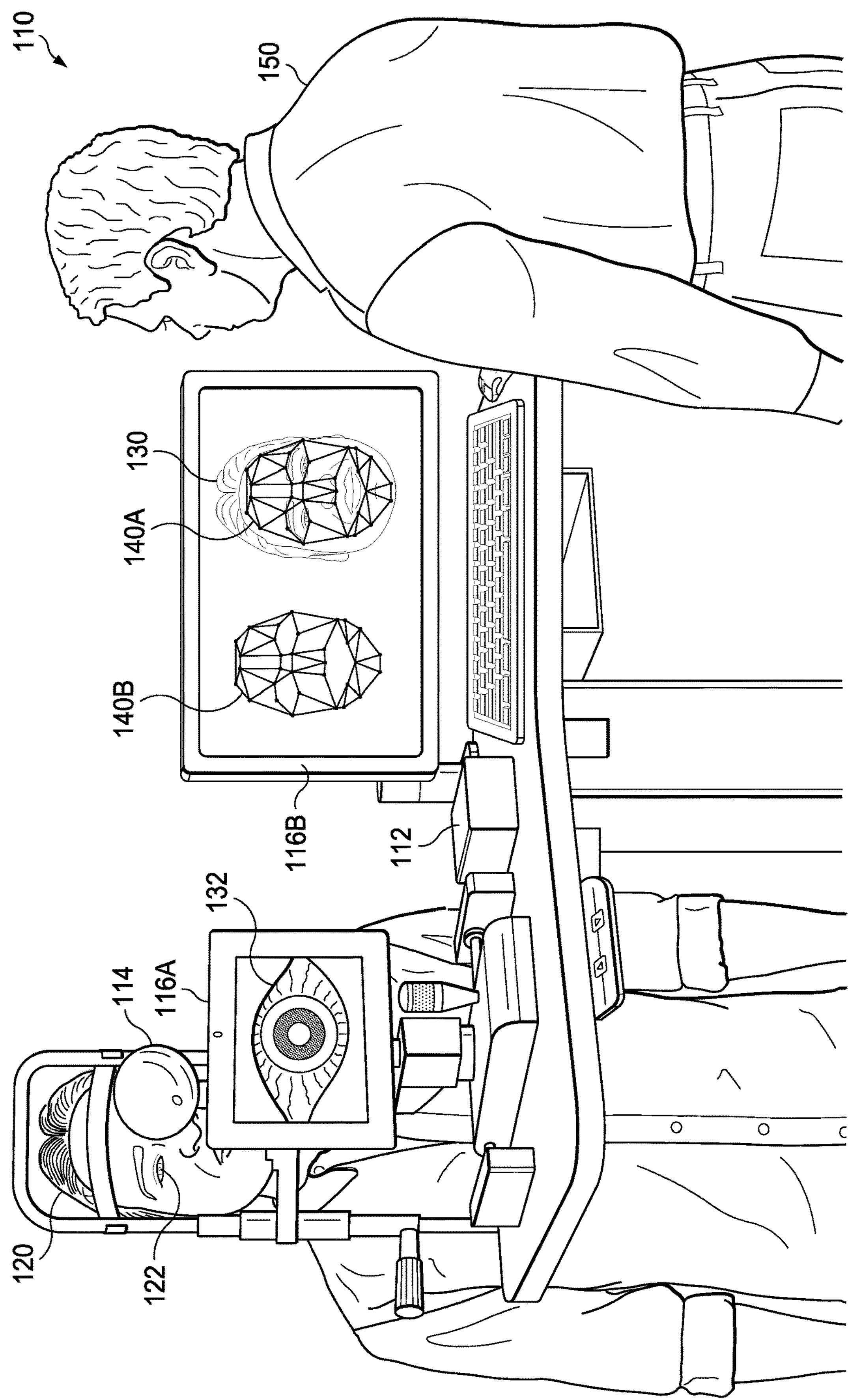
FIG. 1A illustrates an example of a medical system.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

Medical systems may be utilized to identify patients. In one example, a first medical system may be utilized, at a first time, in identifying a patient before a medical procedure. In another example, a second medical system may be utilized, at a second time, in identifying the patient before the medical procedure. The second time may be a later time than the first time. In one example, the first medical system may be utilized at an office of a doctor. In another example, the second medical system may be utilized at a surgical facility.

The first medical system may associate two or more identification attributes associated with the patient. For example, two or more identification attributes associated with the patient may include two or more of a name of the patient, an address of the patient, a telephone number of the patient, a government issued identification number or string of characters of the patient, a date of birth of the patient, a first medical facility identification of the patient, and a first facial identification of the patient, among others. The first facial identification of the patient may be utilized via a facial recognition process, method, and/or system to identify the patient.

The second medical system may associate two or more identification attributes associated with the patient. For example, two or more identification attributes associated with the patient may include two or more of the name of the patient, the address of the patient, the telephone number of the patient, the government issued identification number or string of characters of the patient, the date of birth of the patient, the first medical facility identification of the patient, a second first medical facility identification of the patient, the first facial identification of the patient, and a second facial identification of the patient, among others. The second medical system may utilize a facial recognition process, method, and/or system to obtain the second facial identification of the patient and to determine if the first facial identification of the patient and the second facial identification of the patient match. If the first facial identification of the patient and the second facial identification of the patient match, a medical procedure associated with the patient may proceed. For example, the medical procedure associated with the patient may include a surgical procedure associated with the patient. If the first facial identification of the patient and the second facial identification of the patient do not match, a medical procedure associated with the patient may not proceed. For example, an error or a warning may be issued, which may alert medical personnel that the patient has not been correctly identified.

One or more facial recognition systems, one or more facial recognition methods, and/or one or more facial recognition processes may be utilized in facial identification of a patient. For example, facial recognition may be based at least on identifying a patient by analyzing patterns based at least on one or more textures of a face of the patient and/or one or more shapes of one or more portions of the face of the patient. For example, facial recognition may identify facial features via extracting landmarks and/or features from an image of the face of the patient. One or more landmarks and/or one or more features of the face of the patient may include a relative position, a size, and/or a shape of one or more of eyes, a nose, a cheekbone, and a jaw of the face of the patient. One or more facial recognition systems, one or more facial recognition methods, and/or one or more facial recognition processes may determine data associated with a face of a patient. Data associated with a face of a patient may include a template. For example, a template may be distinguished from a photograph, as a template may include data that may be utilized to distinguish a face of a first patient from a face of a second patient, different from the first patient.

One or more facial recognition systems, one or more facial recognition methods, and/or one or more facial recognition processes may utilize three-dimensional techniques utilizing one or more projectors and/or one or more sensors, among others, to determine information about a shape of the face of the patient. For example, the information about the shape of the face of the patient may be utilized to determine one or more features of a surface of the face of the patient. The one or more features of the surface of the face of the patient may include one or more of a contour of an eye socket, a contour of a nose, and a contour of a chin, among others. An advantage of utilizing three-dimensional facial recognition techniques may be that three-dimensional facial recognition techniques may not be affected by changes in lighting. One or more facial recognition systems, one or more facial recognition methods, and/or one or more facial recognition processes may utilize multiple image sensors. For example, the multiple image sensors may include multiple cameras. A three-dimensional facial recognition technique may utilize multiple image sensors.

A facial recognition system may include one or more image acquisition devices. For example, the one or more image acquisition devices may include one or more cameras. A facial recognition system may include one or more light projectors. In one example, a light projector may project infrared light. In another example, a light projector may include a laser. A facial recognition system may determine locations on a face of the patient. For example, the locations on the face of the patient may be utilized in determining a template of the face of the patient. The template of the face of the patient may be associated with a topography of the face of the patient. The template of the face of the patient may be utilized in facial recognition. For example, the template of the face of the patient may be compared with another template in confirming or disaffirming an identity of the patient. A facial recognition system may include one or more image time of flight (ToF) devices. For example, the one or more time of flight devices may be utilized in determining locations on a face of the patient. A ToF device may include one or more SONAR (sound navigation ranging) devices and/or one or more LIDAR (light imaging, detection, and ranging) devices. For example, a LIDAR device may be utilized in three-dimensional scanning utilizing at least one laser.

A medical procedure associated with the patient may include a portion of the patient (e.g., a site of the medical procedure). For example, the portion of the patient may be similar to another portion of the patient. For example, a right eye of the patient may be similar to a left eye of the patient. The medical procedure associated with the patient may be for the portion of the patient and not the other portion of the patient. For example, the medical procedure associated with the patient may be for right eye of the patient and not for the left eye of the patient. The second medical system may utilize a computer vision process, method, and/or system to determine the portion of the patient from the other portion of the patient. The computer vision process, method, and/or system may utilize a facial recognition process, method, and/or system to determine the portion of the patient from the other portion of the patient. For example, the second medical system may determine that surgical tooling equipment is within an area that is not associated with the portion of the patient. The second medical system may issue a warning or an error if the second medical system determines that surgical tooling equipment is within an area that is not associated with the portion of the patient. In one example, if the medical procedure is for the right eye of the patient (e.g., a site of the medical procedure), the second medical system may issue a warning or an error if the second medical system determines that surgical tooling equipment is within an area that is not associated with the right eye of the patient. In another, if the medical procedure is for the right eye of the patient (e.g., a site of the medical procedure), the second medical system may issue a warning or an error if the second medical system determines that surgical tooling equipment is within an area that is associated with the left eye of the patient.

Turning now to FIG. 1A, an example of a medical system is illustrated. As shown, a medical system 110 may be utilized with a patient 120. As illustrated, medical system 110 may include a computer system 112. Computer system 112 may be communicatively coupled to displays 116A and 116B. As an example, computer system 112 may be integrated with a display 116. Computer system 112 may be communicatively an imaging device 114. In one example, imaging device 114 may include one or more cameras. In another example, imaging device 114 may include a three-dimensional scanner. Imaging device 114 may be utilized in biometry of an eye 122 of patient 120. As shown, display 116A may display biometry information 132 associated with eye 122 of patient 120. As illustrated, display 116B may display an image 130 of patient 120. Computer system 112 may determine facial recognition information. For example, the facial recognition information may include a template of a face of patient 120. As illustrated, a template 140A may be displayed over image 130 of patient 120. For example, display 116B may display template 140A over image 130 of patient 120. As illustrated, a template 140B may be displayed. For example, display 116B may display template 140B. Template 140 may be utilized to identify patient 120. One advantage may include determining biometry information 132 associated with eye 122 of patient 120 and template 140 while patient 120 is being examined by medical system 110. In one example, biometry information 132 associated with eye 122 of patient 120 and template 140 may be determined concurrently. In another example, biometry information 132 associated with eye 122 of patient 120 and template 140 may be determined with a short amount of time with respect to each other.

A person 150 may operate medical system 110. For example, person 150 may be medical personnel. Person 150 may enter identification information associated with patient 120 into computer system 112. The identification information associated with patient 120 may include one or more of a name of patient 120, an address of patient 120, a telephone number of patient 120, a government issued identification number of patient 120, and a date of birth of patient 120, among others. For example, computer system 112 may associate the identification information associated with patient 120 with the facial recognition information. For example, computer system 112 may associate the identification information associated with patient 120 with template 140.

Person 150 may verify one or more portions of the identification information associated with patient 120 before computer system 112 associates the identification information associated with patient 120 with the facial recognition information. For example, one or more portions of the identification information associated with patient 120 may have been stored, via a storage device accessible by computer system 112, before medical system 110 is utilized with patient 120. Person 150 may configure data associated with a portion of patient 120. For example, person 150 may configure data associated with a right eye of patient 120.

Figure 1B:
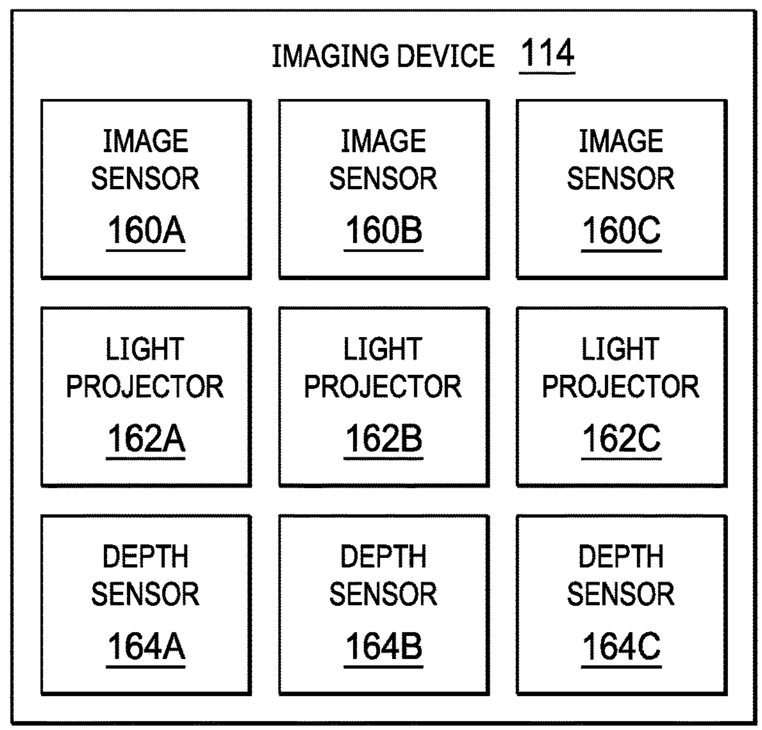
FIG. 1B illustrates an example of an imaging device.
Figure 2A:
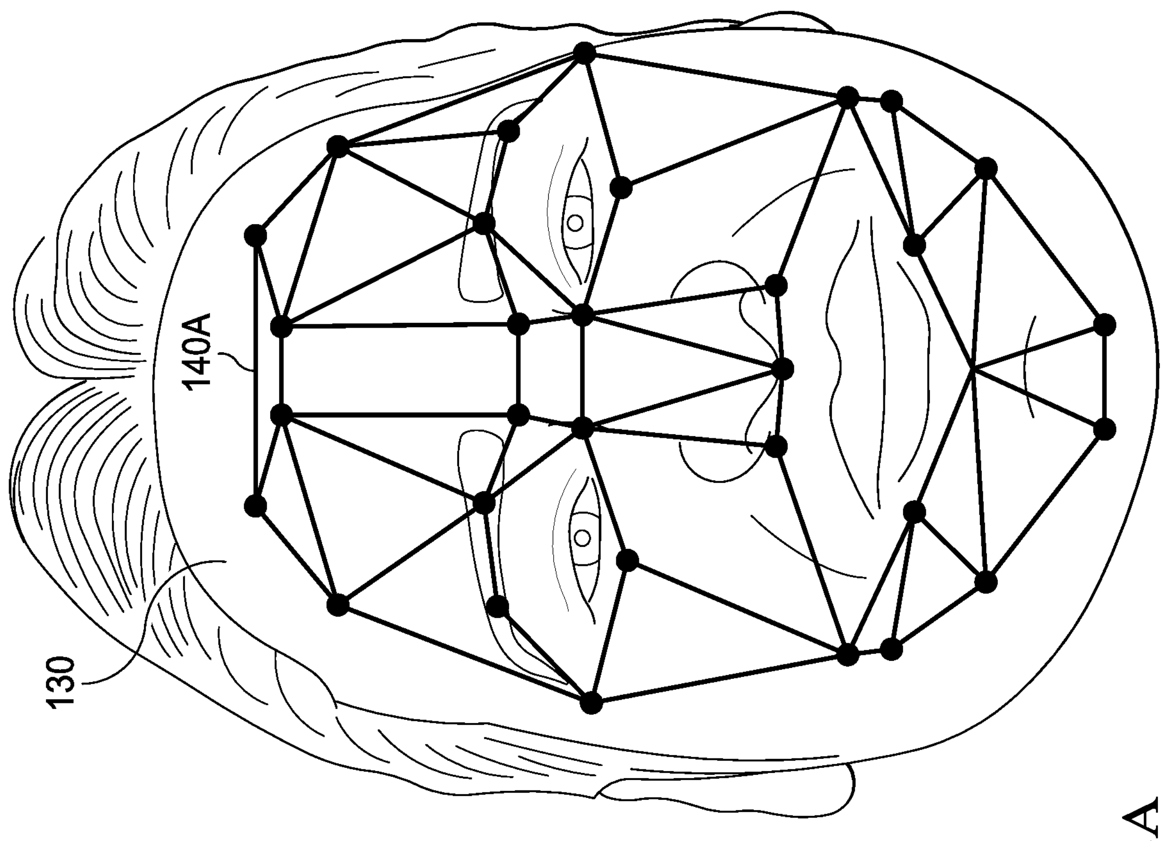
FIGS. 2A and 2B illustrate examples of a template associated with a face of a patient.
Figure 2A:
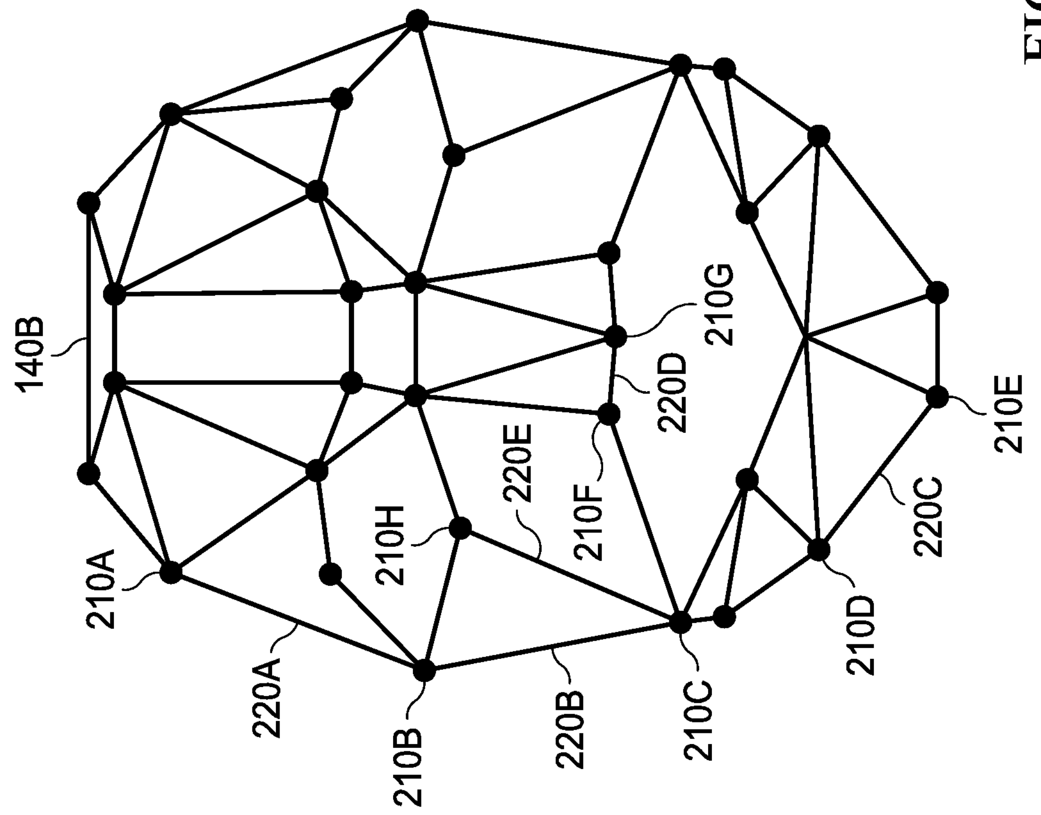
Figure 2B:
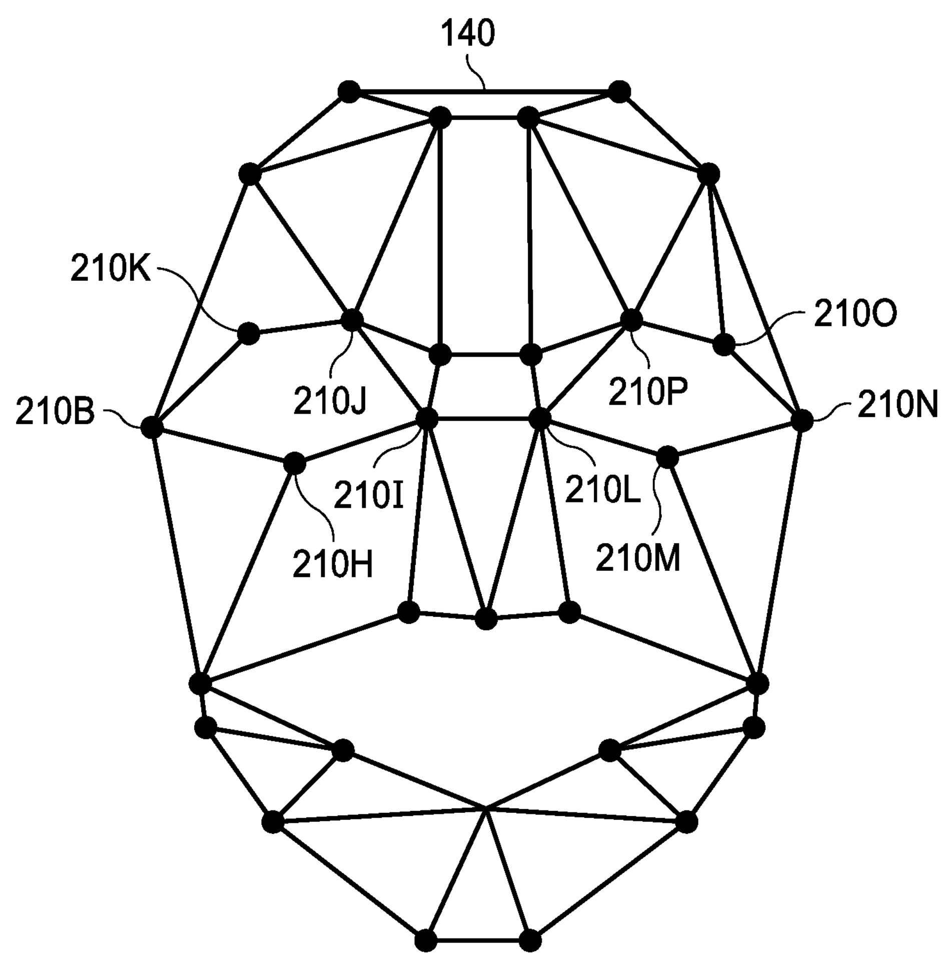

Turning now to FIG. 1B, an example of an imaging device is illustrated. As shown, imaging device 114 may include image sensors 160A-160C. For example, an image sensor 160 may include a camera. As illustrated, imaging device 114 may include light projectors 162A-162C. In one example, a light projector 162 may project visible light. In another example, a light projector 162 may project infrared light. A light projector 162 may project circles and/or dots onto a face of a patient. An image sensor 160 may receive reflections of the circles and/or the dots that were projected onto the face of the patient. A computer system may determine one or more locations and/or one or more templates associated with the face of the patient based at least on the reflections of the circles and/or the dots that were projected onto the face of the patient. As shown, imaging device 114 may include depth sensors 164A-164C. A depth sensor 164 may include a light projector 162. A depth sensor 164 may include an optical sensor. Any two or more of an image sensor 160, a light projector 162, and a depth sensor 164 may be combined. One or more of image sensors 160A-160C, one or more of light projectors 162A-162C, and/or one or more of depth sensors 164A-164C, among others, may produce data that may be utilized to determine locations 210 and/or distances 220, as illustrated in FIGS. 2A and 2B. In one example, computer system 112 may utilize the data to determine locations 210 and/or distances 220, as illustrated in FIGS. 2A and 2B. In another example, computer system 112 may utilize the data to determine a template 140, as illustrated in FIGS. 2A and 2B.

Figure 3A:
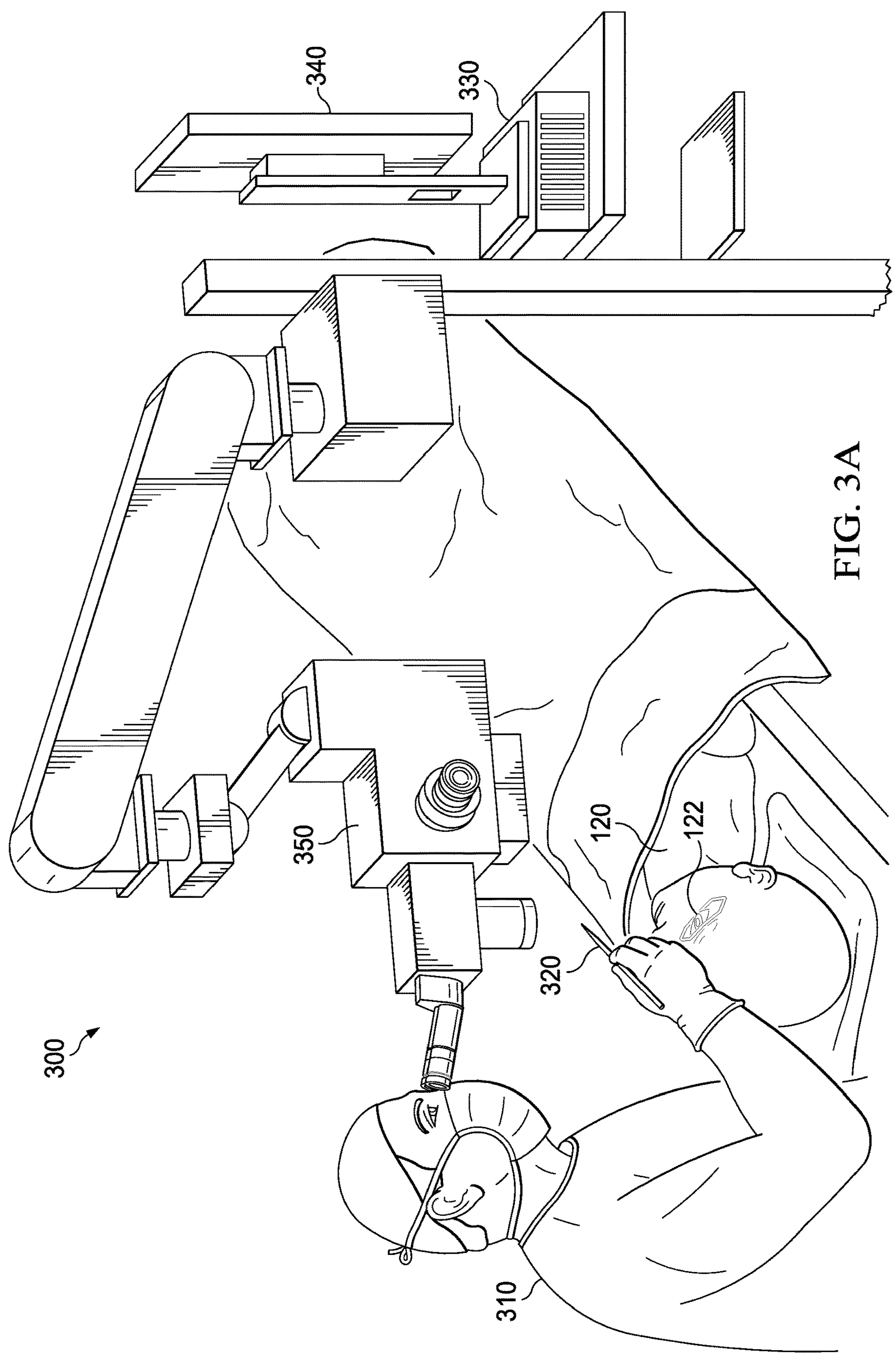
FIG. 3A illustrates an example of another medical system.

Turning now to FIG. 3A, an example of another medical system is illustrated. As shown, a surgeon 310 may utilize surgical tooling equipment 320. In one example, surgeon 310 may utilize surgical tooling equipment 320 in a surgery involving eye 122 of patient 120. Medical system 300 may include an ophthalmic surgical tool tracking system. As illustrated, medical system 300 may include a computer system 330, a display 340, and a microscope 350. Although not specifically illustrated, medical system 300 may include one or more camera systems. As an example, microscope 350 may be or include a microscope integrated display (MID) 352 (illustrated in FIG. 3B). As a second example, microscope 350 may include one or more structures and/or one or more functionalities as those described with reference to MID 352. As a third example, microscope 350 may include a camera system. As another example, microscope 350 may be coupled to a camera system.

Computer system 330 may receive image frames captured by one or more image sensors. For example, computer system 330 may perform various image processing on the one or more image frames. Computer system 330 may perform image analysis on the one or more image frames to identify and/or extract one or more images of surgical tooling equipment 320 from the one or more image frames. Computer system 330 may generate a graphical user interface (GUI), which may overlay the one or more image frames. For example, the GUI may include one or more indicators and/or one or more icons, among others. The one or more indicators may include surgical data, such as one or more positions and/or one or more orientations. The one or more indicators may include one or more warnings. The GUI may be displayed by display 340 and/or microscope 350 to surgeon 310 and/or other medical personnel.

Computer system 330, display 340, and microscope 350 may be implemented in separate housings communicatively coupled to one another or within a common console or housing. A user interface may be associated with one or more of computer system 330, display 340, and microscope 350, among others. For example, a user interface may include one or more of a keyboard, a mouse, a joystick, a touchscreen, an eye tracking device, a speech recognition device, a gesture control module, dials, and/or buttons, among other input devices. A user (e.g., surgeon 310 and/or other medical personnel) may enter desired instructions and/or parameters via the user interface. For example, the user interface may be utilized in controlling one or more of computer system 330, display 340, and microscope 350, among others.

Figure 3B:
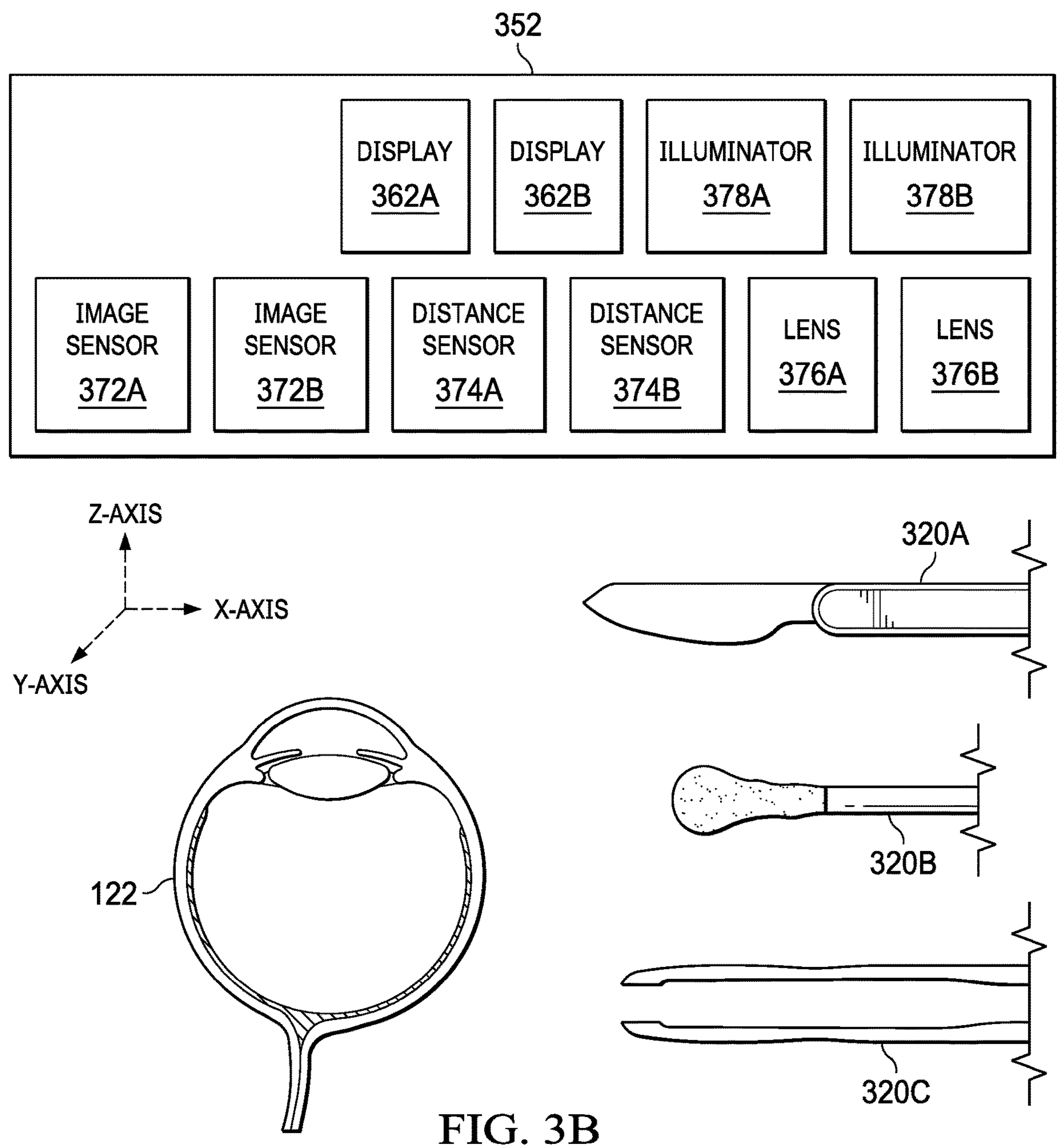
FIG. 3B illustrates an example of a microscope integrated display and examples of surgical tooling equipment.

Turning now to FIG. 3B, an example of a microscope integrated display and examples of surgical tooling equipment are illustrated. As shown, surgical tooling equipment 320A may be or include a scalpel. As illustrated, surgical tooling equipment 320B may be or include a Q-tip. As shown, surgical tooling equipment 320C may be or include tweezers. Other surgical tooling equipment that is not specifically illustrated may be utilized with one or more systems, one or more processes, and/or one or more methods described herein.

As an example, surgical tooling equipment 320 may be marked with one or more patterns. The one or more patterns may be utilized in identifying surgical tooling equipment 320. The one or more patterns may include one or more of a hash pattern, a stripe pattern, and a fractal pattern, among others. As another example, surgical tooling equipment 320 may be marked with a dye and/or a paint. The dye and/or the paint may reflect one or more of visible light, infrared light, and ultraviolet light, among others. In one example, an illuminator 378 may provide ultraviolet light, and image sensor 372 may receive the ultraviolet light reflected from surgical tooling equipment 320. Computer system 330 may receive image data, based at least on the ultraviolet light reflected from surgical tooling equipment 320, from image sensor 372 and may utilize the image data, based at least on the ultraviolet light reflected from surgical tooling equipment 320, to identify surgical tooling equipment 320 from other image data provided by image sensor 372. In another example, an illuminator 378 may provide infrared light, and image sensor 372 may receive the infrared light reflected from surgical tooling equipment 320. Computer system 330 may receive image data, based at least on the infrared light reflected from surgical tooling equipment 320, from image sensor 372 and may utilize the image data, based at least on the infrared light reflected from surgical tooling equipment 320, to identify surgical tooling equipment 320 from other image data provided by image sensor 372.

As illustrated, MID 352 may include displays 362A and 362B. For example, surgeon 310 may look into multiple eye pieces, and displays 362A and 362B may display information to surgeon 310. Although MID 352 is shown with multiple displays, MID 352 may include a single display 362. For example, MID 352 may be implemented with one or more displays 362. As shown, MID 352 may include image sensors 372A and 372B. In one example, image sensors 372A and 372B may acquire images. In a second example, image sensors 372A and 372B may include cameras. In another example, an image sensor 372 may acquire images via one or more of visible light, infrared light, and ultraviolet light, among others. One or more image sensors 372A and 372B may provide data of images to computer system 330. Although MID 352 is shown with multiple image sensors, MID 352 may include a single image sensor 372. For example, MID 352 may be implemented with one or more image sensors 372.

As illustrated, MID 352 may include distance sensors 374A and 374. For example, a distance sensor 374 may determine a distance to surgical tooling equipment 320. Distance sensor 374 may determine a distance associated with a Z-axis. Although MID 352 is shown with multiple image sensors, MID 352 may include a single distance sensor 374. In one example, MID 352 may be implemented with one or more distance sensors 374. In another example, MID 352 may be implemented with no distance sensor. As shown, MID 352 may include lenses 376A and 376B. Although MID 352 is shown with multiple lenses 376A and 376B, MID 352 may include a single lens 376. For example, MID 352 may be implemented with one or more lenses 376. As illustrated, MID 352 may include illuminators 378A and 378B. For example, an illuminator 378 may provide and/or produce one or more of visible light, infrared light, and ultraviolet light, among others. Although MID 352 is shown with multiple illuminators, MID 352 may include a single illuminator 378. For example, MID 352 may be implemented with one or more illuminators 378. MID 352 may include one or more structures and/or one or more functionalities as those described with reference to imaging device 114. MID 352 may include a computer system. For example, the computer system of MID 352 may implement at least a portion of one or more systems, one or more processes, one or more methods, and/or one or more flowcharts described herein.

Figure 4D:
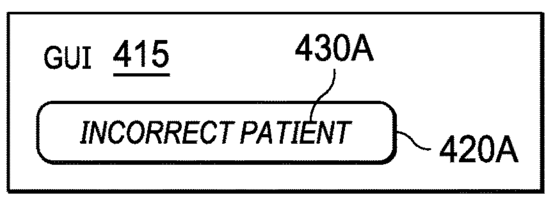
FIG. 4D illustrates an example of a graphical user interface that provides a warning or an error.
Figure 4E:
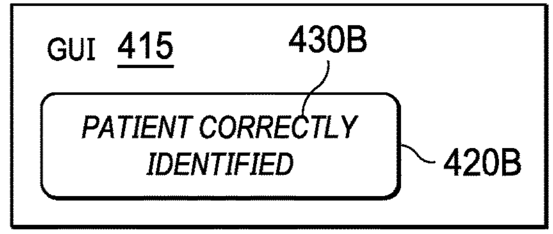
FIG. 4E illustrates an example of a graphical user interface that provides an indication that a patient has been correctly identified.
Figure 4A:
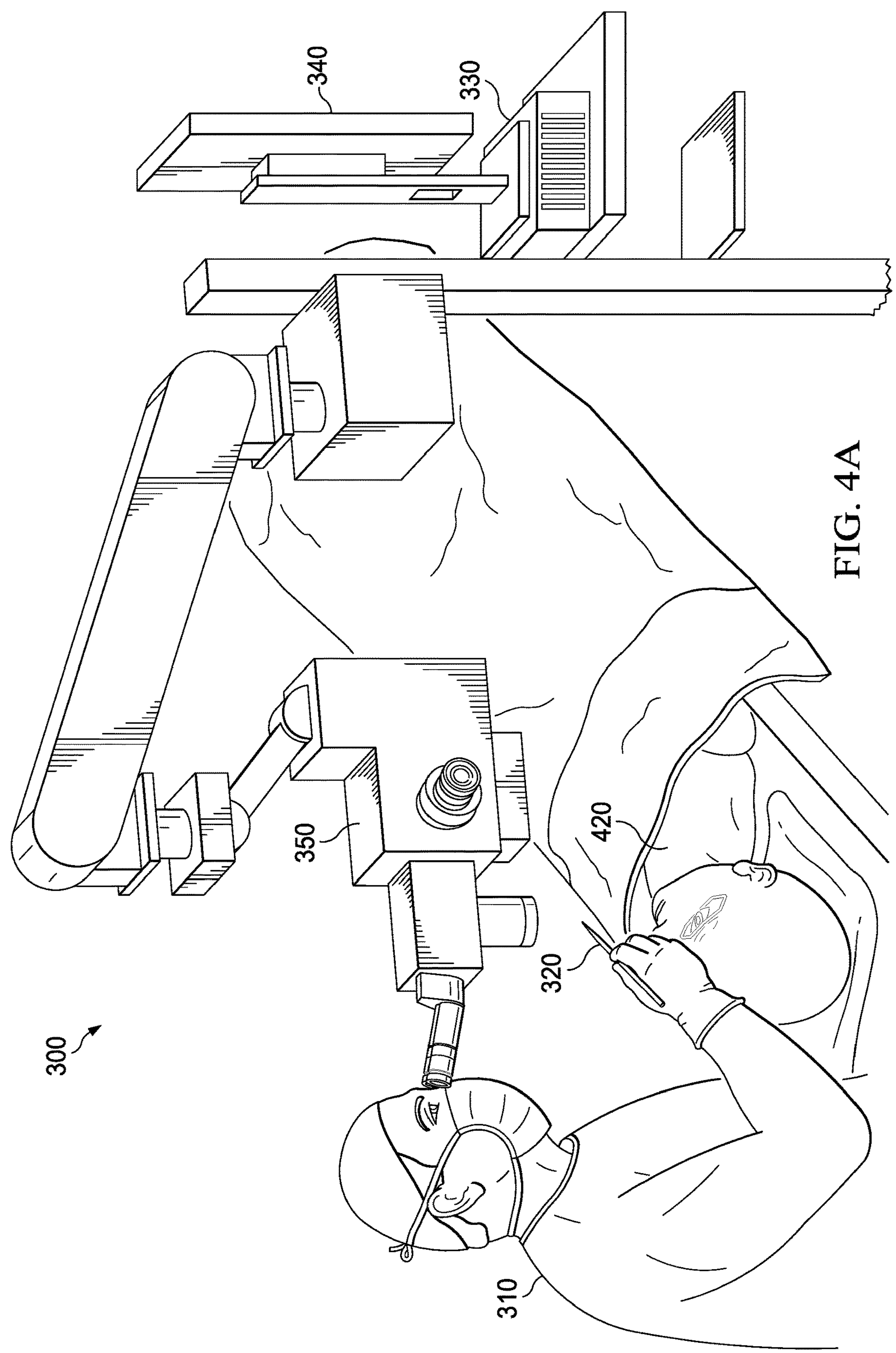
FIGS. 4A-4C illustrate examples of identifying a patient.
Figure 4B:
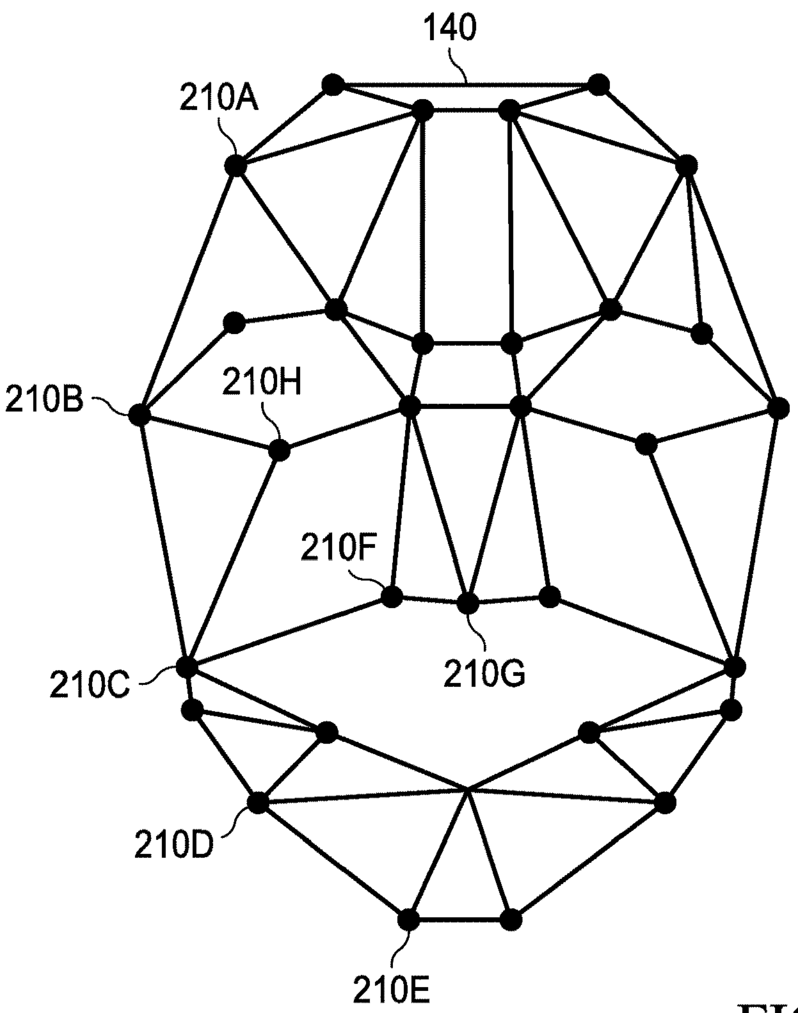
Figure 4B:
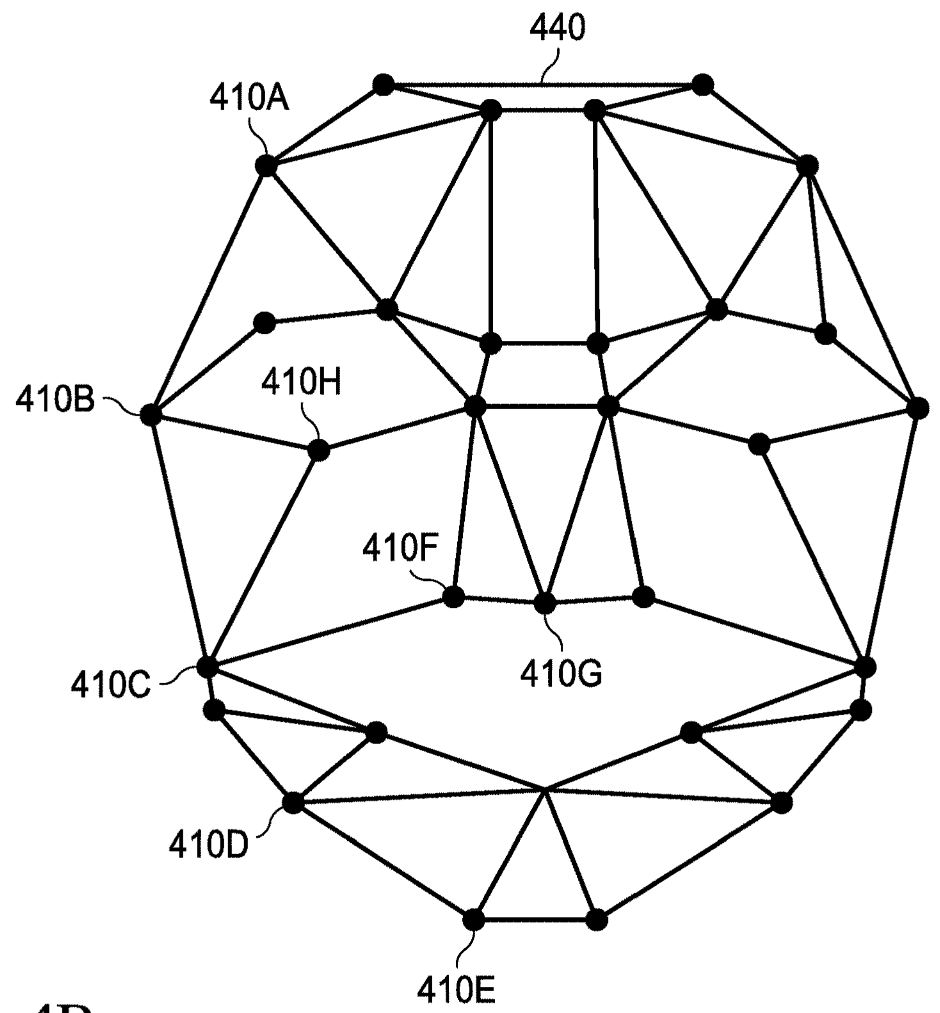
Figure 4C:
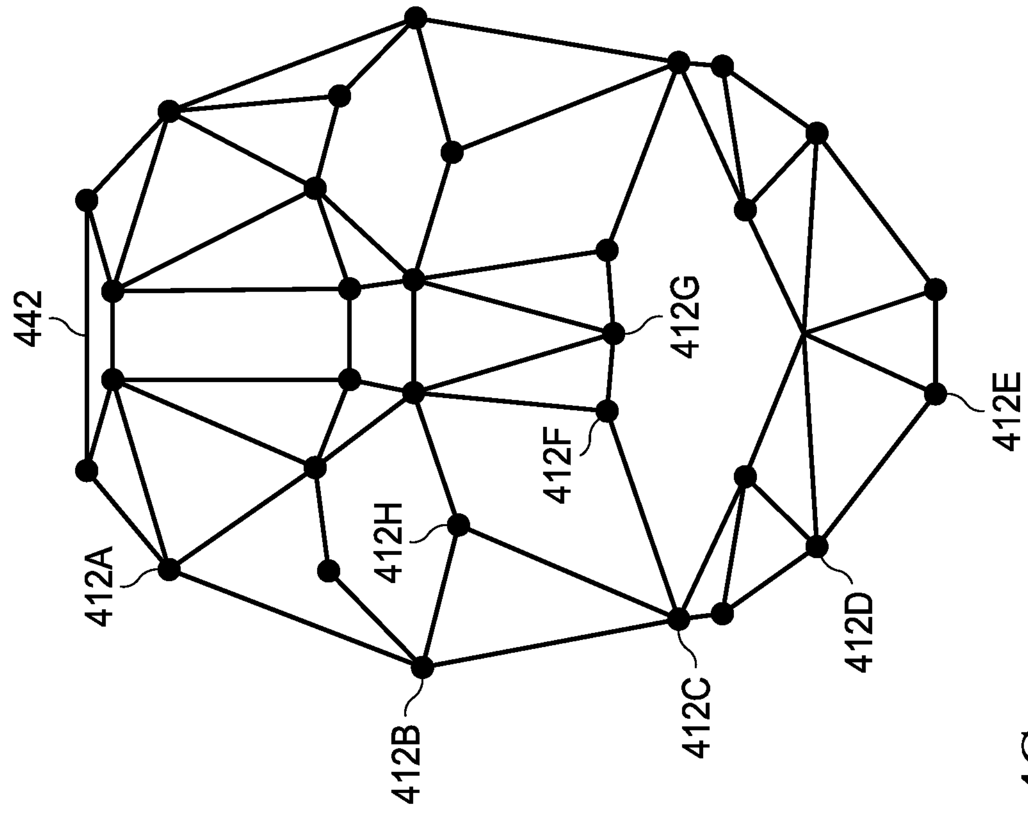
Figure 4C:
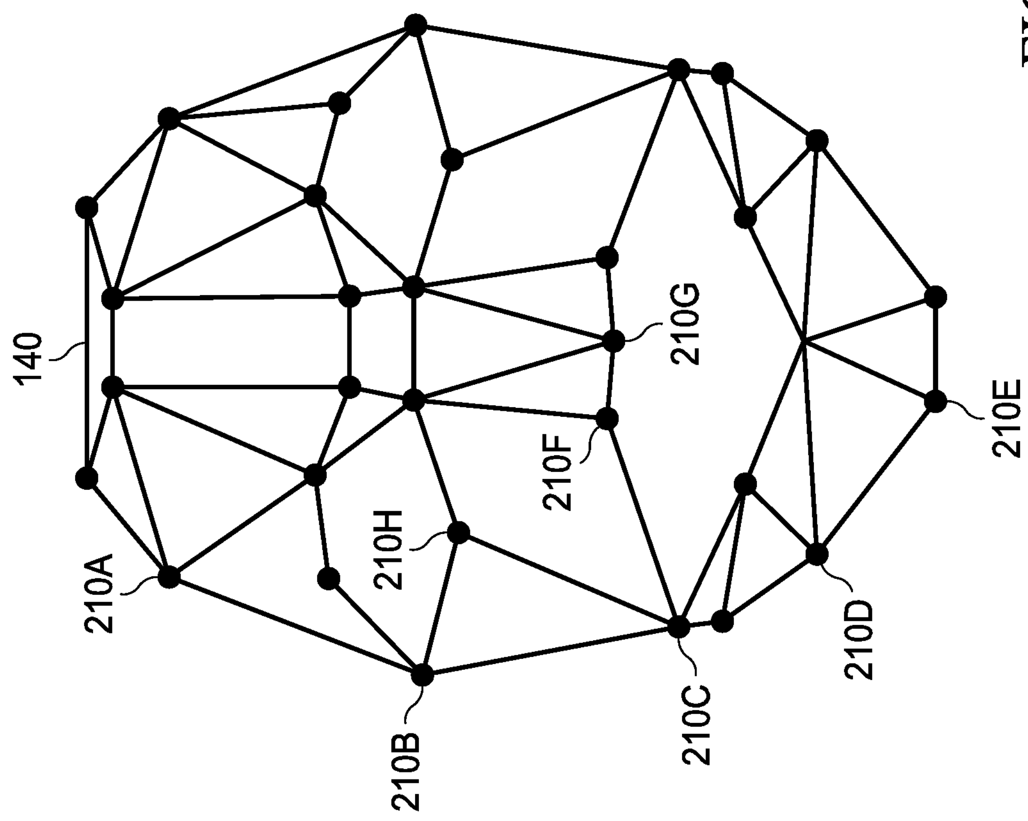

Turning now to FIGS. 4A-4C, examples of identifying a patient is illustrated. As shown, surgeon 310 may be prepared to operate on a patient 420. For example, patient 420 may be an incorrect patient for an operation that surgeon 310 may be prepared to perform. Patient 120 may be a correct patient for an operation that surgeon 310 may be prepared to perform. Patient 420 may be identified via facial recognition. For example, a template 440 may be determined based at least on locations 410 associated, illustrated in FIG. 4B, with a face of patient 420. Computer system 330 may determine template 440. A computer system of microscope 350 may determine template 440.

Template 440 may be determined not to match template 140. For example, a patient associated with template 140 may be the expected patient for the surgery. If template 440 is determined not to match template 140, a warning or an error may be issued. In one example, determining that template 440 does not match template 140 may include determining that one or more positions 210 do not match one or more positions 410. In another example, determining that template 440 does not match template 140 may include determining that a polygon formed by three or more locations 410 does not match a polygon formed by three or more locations 210. The three or more locations 410 may correspond to three or more locations 210. For example, three or more locations 410B, 410C, and 410H may correspond to locations 210B, 210C, and 210H. A polygon formed by locations 410B, 410C, and 410H may not match a polygon formed by locations 210B, 210C, and 210H. Computer system 330 may determine template 440 and template 140 do not match. Microscope 350 may determine template 440 and template 140 do not match. MID 352 may determine template 440 and template 140 do not match.

As shown, in FIG. 3A, surgeon 310 may be prepared to operate on a patient 120. For example, patient 120 may be a correct patient for an operation that surgeon 310 may be prepared to perform. Patient 120 may be identified via facial recognition. For example, a template 442 may be determined based at least on locations 412, as illustrated in FIG. 4C. Computer system 330 may determine template 442. A computer system of microscope 350 may determine template 442. A computer system of MID 352 may determine template 442.

Template 442 may be determined to match template 140. For example, a patient associated with template 140 may be the expected patient for the surgery. If template 442 is determined to match template 140, an indication that the surgery may proceed may be issued. In one example, determining that template 442 does match template 140 may include determining that one or more positions 210 do match one or more positions 412. In another example, determining that template 442 does match template 140 may include determining that a polygon formed by three or more locations 412 does match a polygon formed by three or more locations 210. The three or more locations 412 may correspond to three or more locations 210. For example, three or more locations 412B, 412C, and 412H may correspond to locations 210B, 210C, and 210H. A polygon formed by locations 412B, 412C, and 412H may match a polygon formed by locations 210B, 210C, and 210H. Computer system 330 may determine that template 442 and template 140 do match. Microscope 350 may determine that template 442 and template 140 do match. MID 352 may determine that template 442 and template 140 do match.

A GUI 415, illustrated in FIG. 4D, may provide the warning or the error that an incorrect patient has been identified. In one example, the warning or the error may include an icon 420A. In a second example, the warning or the error may include text 430A, which may indicate that an incorrect patient has been detected. GUI 415 may be displayed via display 340, microscope 350, and/or MID 352. In another example, the warning or the error may include one or more audible sounds. GUI 415, illustrated in FIG. 4E, may provide the indication that the patient has been correctly identified. In one example, the indication may include an icon 420B. In another example, the indication may include text 430B, which may indicate that the patient has been correctly identified. GUI 415 may be displayed via display 340, microscope 350, and/or MID 352.

Figure 5A:
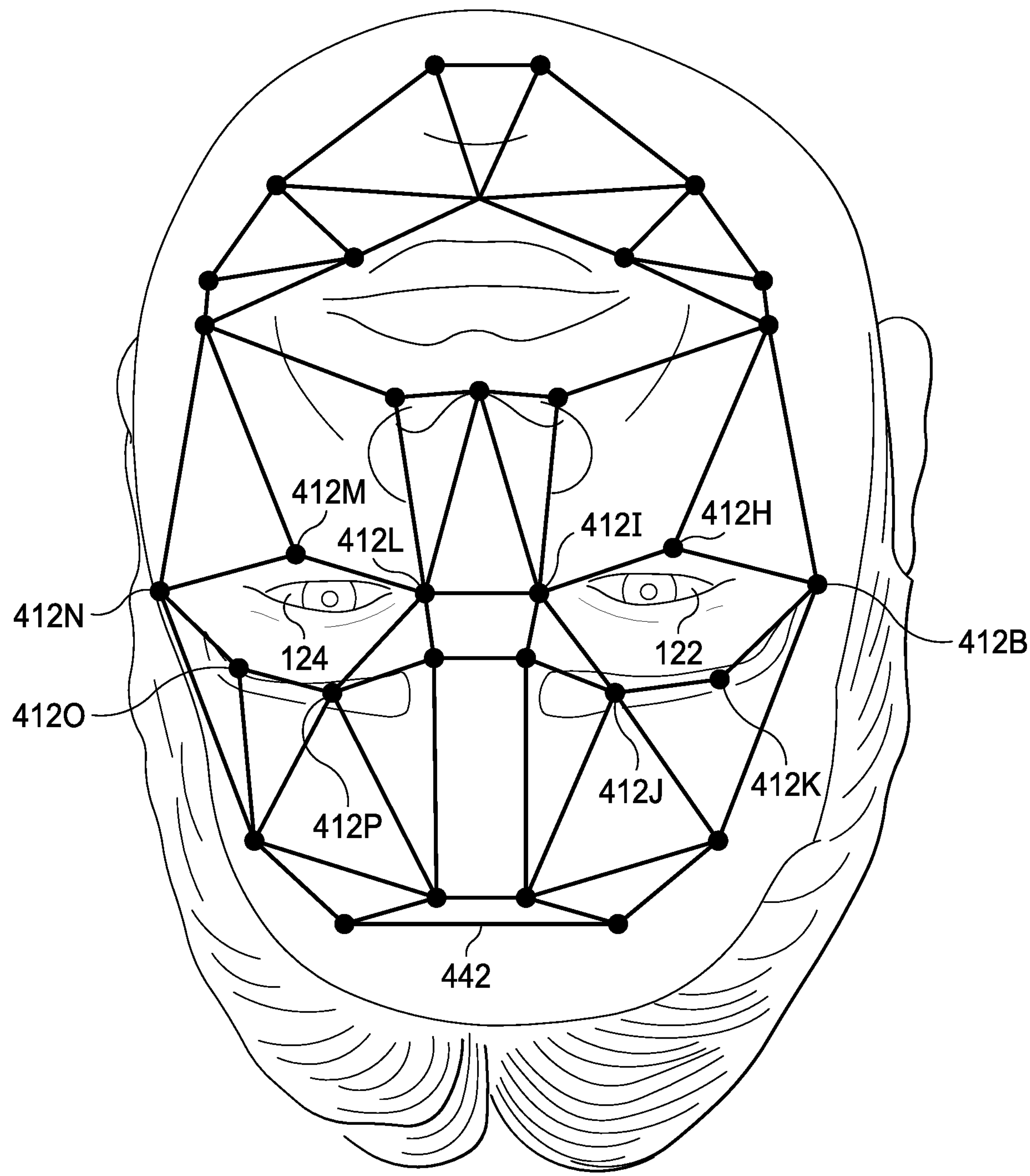
FIG. 5A illustrates an example of an area of a surgical procedure.

Turning now to FIG. 5A, an example of an area of a surgical procedure is illustrated. As shown, an area may be bounded by locations 412B and 412H-412K. As illustrated, the area bounded by locations 412B and 412H-412K may include eye 122. For example, a surgical procedure may be performed on eye 122. As shown, an area may be bounded by locations 412L-412P. As illustrated, the area bounded by locations 412L-412P may include an eye 124. For example, a surgical procedure may not be performed on eye 124.

Figure 5B:
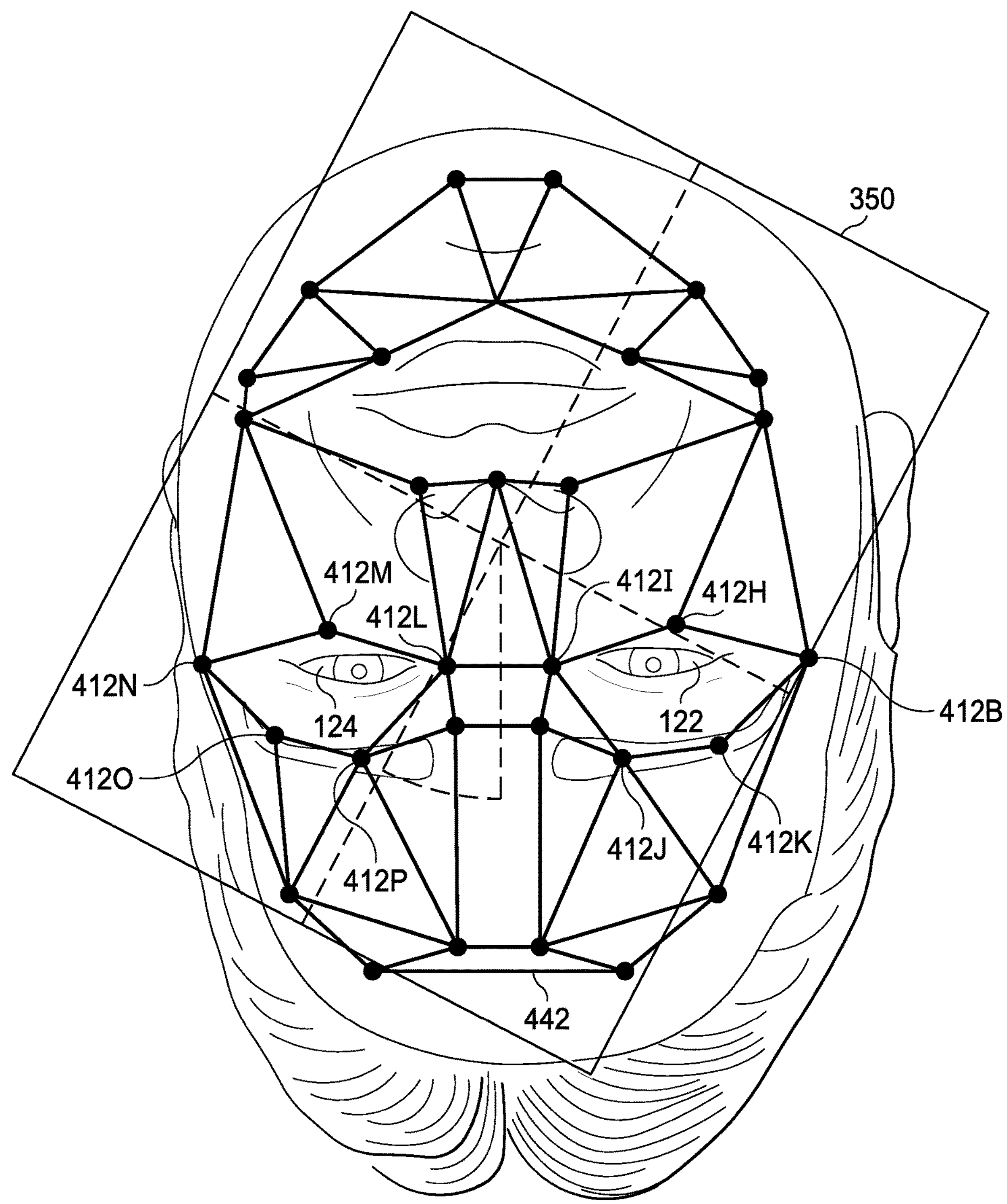
FIG. 5B illustrates an example of determining a position of a microscope.

Turning now to FIG. 5B, an example of determining a position of a microscope is illustrated. As shown, microscope 350 may be at an angle to template 442. In one example, computer system 330 may determine an angle between microscope 350 and template 442. In another example, microscope 350 may determine an angle between microscope 350 and template 442. Microscope 350 may include a computer system. For example, the computer system of microscope 350 may determine an angle between microscope 350 and template 442.

Figure 5C:
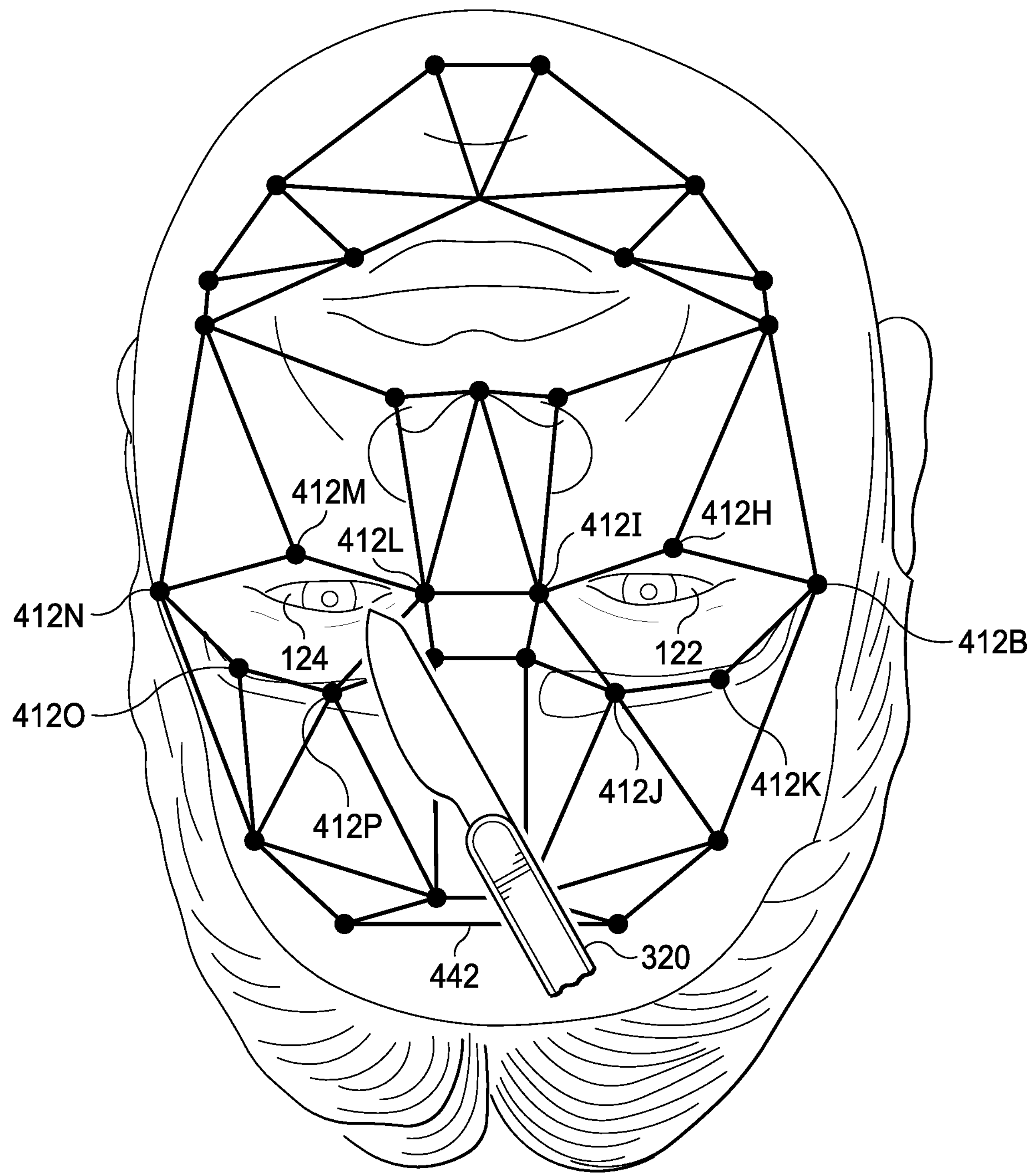
FIG. 5C illustrates an example of determining that surgical tooling equipment is included in an area.

Turning now to FIG. 5C, an example of determining that surgical tooling equipment is included in an area is illustrated. As shown, surgical tooling equipment 320 may be included in the area bounded by locations 412L-412P. In one example, a surgical procedure may not be performed on eye 124. In another example, a surgical procedure may not be performed within the area bounded by locations 412L-412P.

Computer system 330 may determine that surgical tooling equipment 320 is included in the area bounded by locations 412L-412P. For example, computer system 330 may provide a warning that surgical tooling equipment 320 is included in the area bounded by locations 412L-412P. A GUI 510, illustrated in FIG. 5E, may provide the warning that surgical tooling equipment 320 is included in the area bounded by locations 412L-412P. In one example, the warning may include an icon 520A. In a second example, the warning may include text 530A, which may indicate that surgical tooling equipment 320 has been detected in a wrong or incorrect area. GUI 510 may be displayed via display 340, microscope 350, and/or MID 352. In another example, the warning may include one or more audible sounds.

Microscope 350 may determine that surgical tooling equipment 320 is included in the area bounded by locations 412L-412P. For example, microscope 350 may provide a warning that surgical tooling equipment 320 is included in the area bounded by locations 412L-412P. MID 352 may determine that surgical tooling equipment 320 is included in the area bounded by locations 412L-412P. For example, MID 352 may provide a warning that surgical tooling equipment 320 is included in the area bounded by locations 412L-412P. GUI 510, illustrated in FIG. 5E, may provide the warning that surgical tooling equipment 320 is included in the area bounded by locations 412L-412P. In one example, the warning may include an icon 520A. In a second example, the warning may include text 530A, which may indicate that surgical tooling equipment 320 has been detected in a wrong or incorrect area. GUI 510 may be displayed via display 340, microscope 350, and/or MID 352. In another example, the warning may include one or more audible sounds.

Figure 5D:
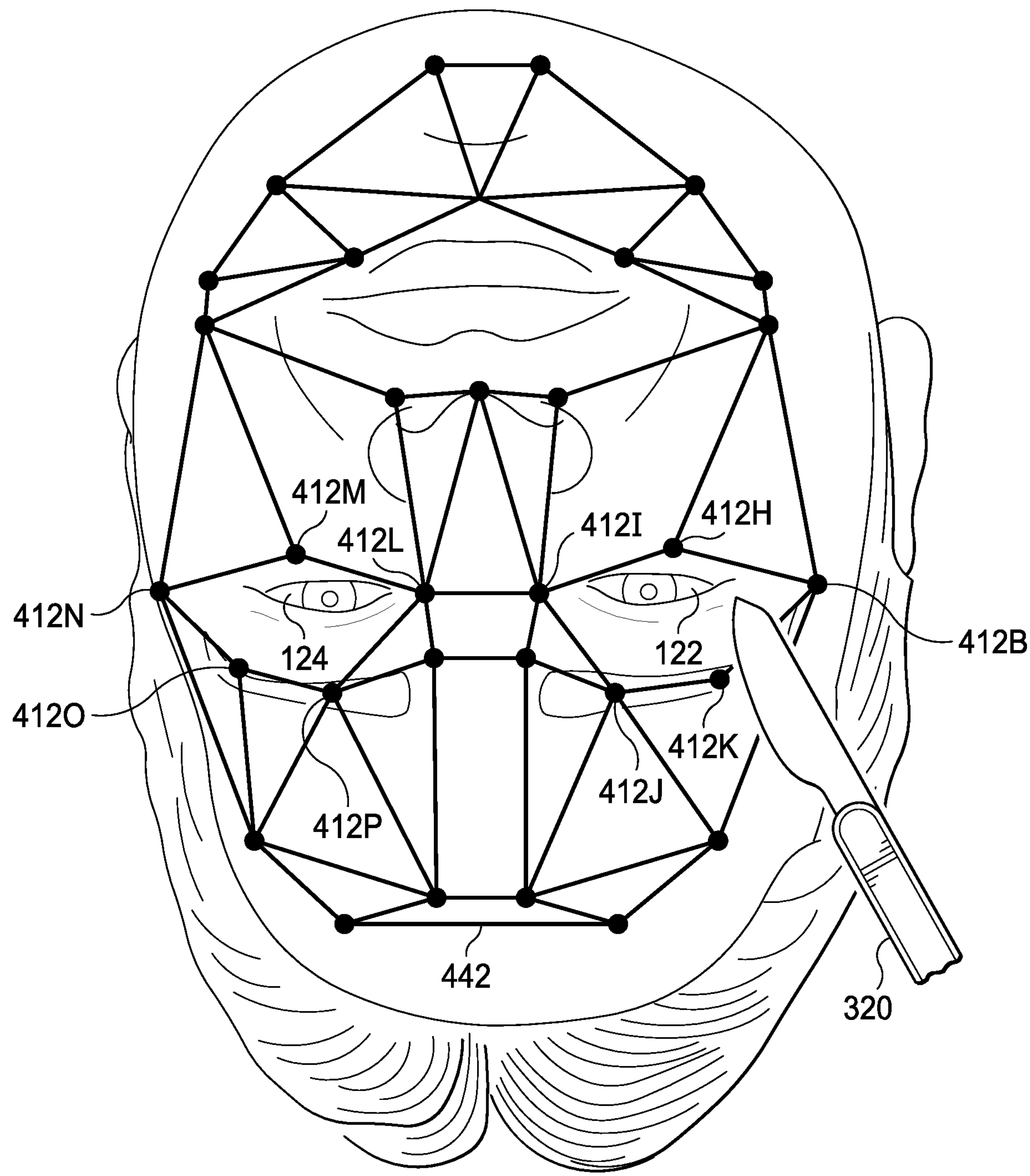
FIG. 5D illustrates another example of determining that surgical tooling equipment is included in an area.
Figure 5E:
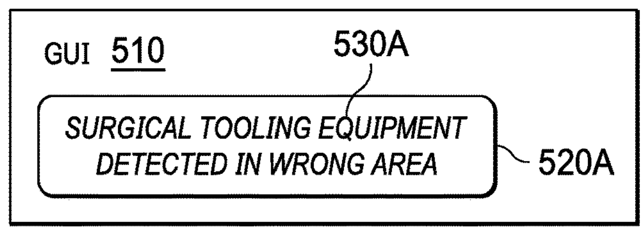
FIG. 5E illustrates an example of a graphical user interface that provides a warning.

Turning now to FIG. 5D, another example of determining that surgical tooling equipment is included in an area is illustrated. As shown, surgical tooling equipment 320 may be included in the area bounded by locations 412B and 412H-412K. In one example, a surgical procedure may be performed on eye 122. In another example, a surgical procedure may be performed within the area bounded by locations 412B and 412H-412K.

Figure 5F:
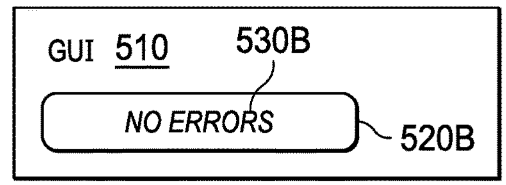
FIG. 5F illustrates an example of a graphical user interface that provides an indication that no errors have been detected.

Computer system 330 may determine that surgical tooling equipment 320 is included in the area bounded by locations 412B and 412H-412K. For example, computer system 330 may provide an indication that surgical tooling equipment 320 is included in the area bounded by locations 412B and 412H-412K. GUI 510, illustrated in FIG. 5F, may provide the indication that surgical tooling equipment 320 is included in the area bounded by locations 412B and 412H-412K. In one example, the indication may include an icon 520B. In another example, the indication may include text 530B, which may indicate that no errors have been detected. GUI 510 may be displayed via display 340, microscope 350, and/or MID 352.

Microscope 350 may determine that surgical tooling equipment 320 is included in the area bounded by locations 412B and 412H-412K. For example, microscope 350 may provide an indication that surgical tooling equipment 320 is included in the area bounded by locations 412B and 412H-412K. MID 352 may determine that surgical tooling equipment 320 is included in the area bounded by locations 412B and 412H-412K. For example, MID 352 may provide an indication that surgical tooling equipment 320 is included in the area bounded by locations 412B and 412H-412K. GUI 510, illustrated in FIG. 5F, may provide the indication that surgical tooling equipment 320 is included in the area bounded by locations 412B and 412H-412K. In one example, the indication may include an icon 520B. In another example, the indication may include text 530B, which may indicate that no errors have been detected. GUI 510 may be displayed via display 340, microscope 350, and/or MID 352.

Figure 6:
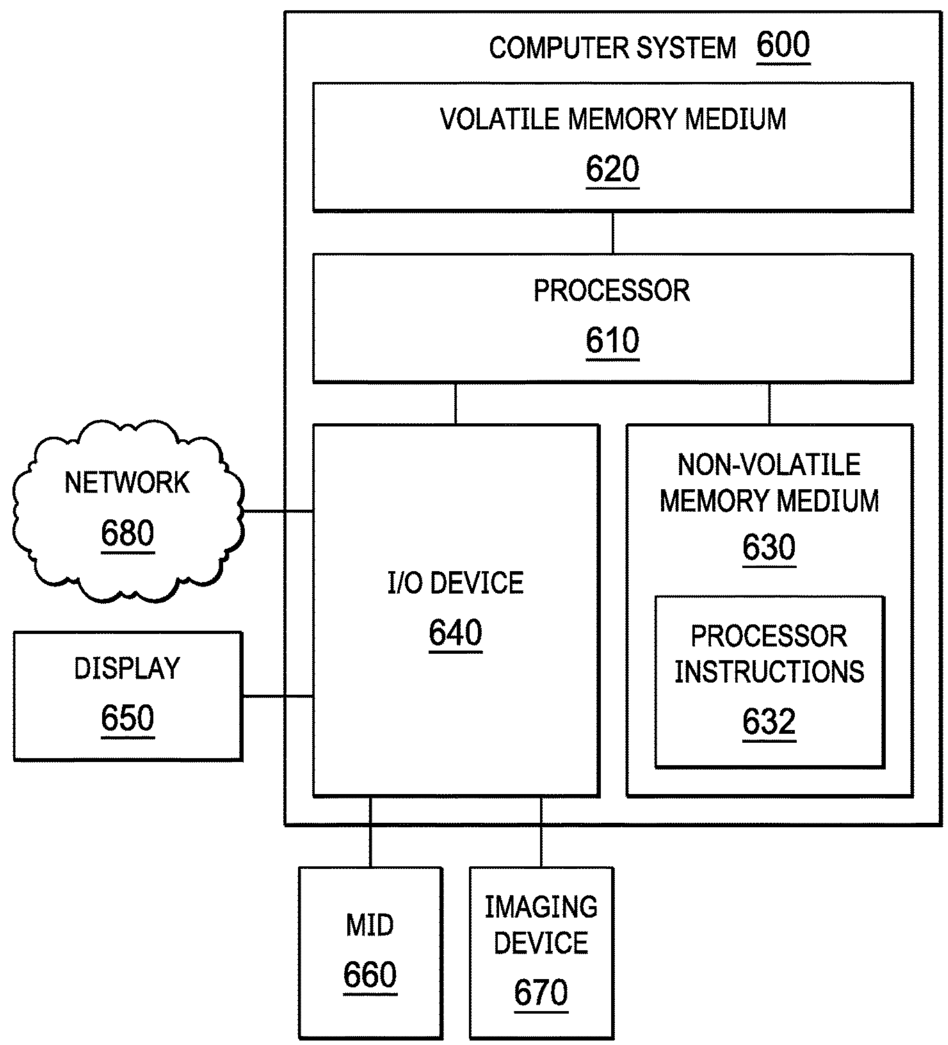
FIG. 6 illustrates an example of a computer system.

Turning now to FIG. 6, an example of a computer system is illustrated. As shown, a computer system 600 may include a processor 610, a volatile memory medium 620, a non-volatile memory medium 630, and an input/output (I/O) device 640. As illustrated, volatile memory medium 620, non-volatile memory medium 630, and I/O device 640 may be communicatively coupled to processor 610.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 630 may include processor instructions 632. Processor instructions 632 may be executed by processor 610. In one example, one or more portions of processor instructions 632 may be executed via non-volatile memory medium 630. In another example, one or more portions of processor instructions 632 may be executed via volatile memory medium 620. One or more portions of processor instructions 632 may be transferred to volatile memory medium 620.

Processor 610 may execute processor instructions 632 in implementing at least a portion of one or more systems, one or more flow charts, one or more processes, and/or one or more methods described herein. For example, processor instructions 632 may be configured, coded, and/or encoded with instructions in accordance with at least a portion of one or more systems, one or more flowcharts, one or more methods, and/or one or more processes described herein. Although processor 610 is illustrated as a single processor, processor 610 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 610 may include any suitable system, device, or apparatus operable to interpret and execute program instructions, process data, or both stored in a memory medium and/or received via a network. Processor 610 further may include one or more microprocessors, microcontrollers, digital signal processors (DSPs), application specific integrated circuits (ASICs), or other circuitry configured to interpret and execute program instructions, process data, or both.

I/O device 640 may include any instrumentality or instrumentalities, which allow, permit, and/or enable a user to interact with computer system 600 and its associated components by facilitating input from a user and output to a user. Facilitating input from a user may allow the user to manipulate and/or control computer system 600, and facilitating output to a user may allow computer system 600 to indicate effects of the user's manipulation and/or control. For example, I/O device 640 may allow a user to input data, instructions, or both into computer system 600, and otherwise manipulate and/or control computer system 600 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 640 may include one or more busses, one or more serial devices, and/or one or more network interfaces, among others, that may facilitate and/or permit processor 610 to implement at least a portions of one or more systems, processes, and/or methods described herein. In one example, I/O device 640 may include a storage interface that may facilitate and/or permit processor 610 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 640 may include a network interface that may facilitate and/or permit processor 610 to communicate with a network. I/O device 640 may include one or more of a wireless network interface and a wired network interface. In a third example, I/O device 640 may include one or more of a peripheral component interconnect (PCI) interface, a PCI Express (PCIe) interface, a serial peripheral interconnect (SPI) interface, and an inter-integrated circuit ($I^2C$) interface, among others. In a fourth example, I/O device 640 may include circuitry that may permit processor 610 to communicate data with one or more sensors. In another example, I/O device 640 may facilitate and/or permit processor 610 to communicate data with one or more of a display 650, a MID 660, and an imaging device 670, among others. One or more of display 650, MID 660, and imaging device 670, among others, may be coupled to processor 610 via I/O device 640. As illustrated, I/O device 640 may be coupled to a network 680. For example, I/O device 640 may include a network interface.

Network 680 may include a wired network, a wireless network, an optical network, or a combination of the foregoing, among others. Network 680 may include and/or be coupled to various types of communications networks. For example, network 680 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

A computer system described herein may include one or more structures and/or one or more functionalities as those described with reference to computer system 600. In one example, computer system 112 may include one or more structures and/or one or more functionalities as those described with reference to computer system 600. In a second example, computer system 330 may include one or more structures and/or one or more functionalities as those described with reference to computer system 600. In a third example, a computer system of microscope 350 may include one or more structures and/or one or more functionalities as those described with reference to computer system 600. In another example, a computer system of MID 352 may include one or more structures and/or one or more functionalities as those described with reference to computer system 600.

Figure 7:
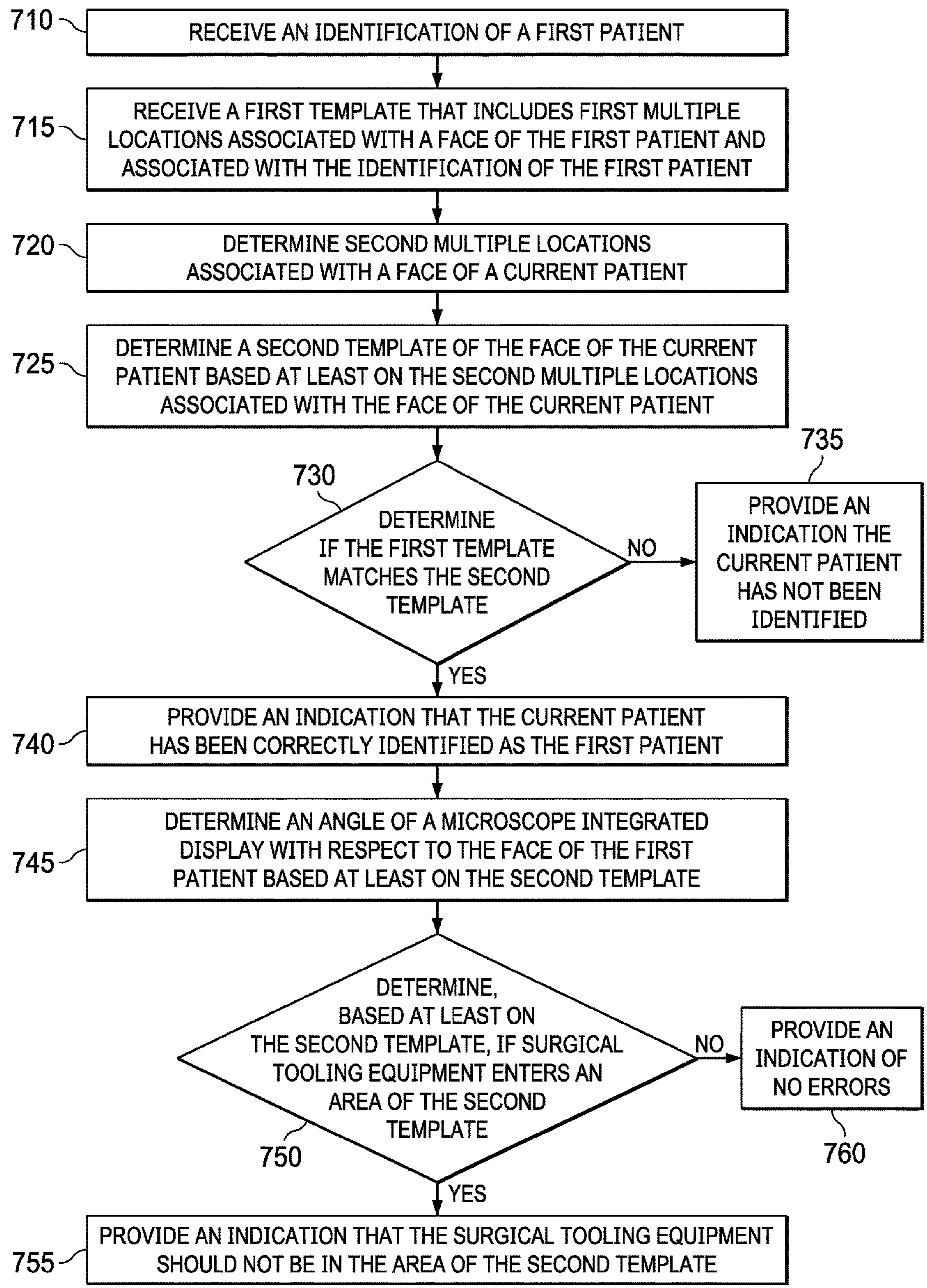
FIG. 7 illustrate an example of a method of operating a system.

Turning now to FIG. 7, an example of a method of operating a system is illustrated. At 710, an identification of a first patient may be received. For example, computer system 330 may receive an identification of a first patient. The first patient may be patient 120. The identification of the first patient may include a name of the first patient. The identification of the first patient may include a number or a string of characters associated with the first patient.

At 715, a first template that includes first multiple locations associated with a face of the first patient and associated with the identification of the first patient may be received. For example, computer system 330 may receive a first template that includes first multiple locations associated with a face of the first patient and associated with the identification of the first patient. For example, computer system 330 may receive template 140. Computer system 330 may retrieve the first template based at least on the identification of the first patient. In one example, computer system 330 may retrieve and/or receive the first template from a storage device. In another example, computer system 330 may retrieve and/or receive the first template from a network. Receiving the first template that includes the first multiple locations associated with the face of the first patient may include receiving medical information associated with the first patient. For example, the medical information may include biometry information associated with the first patient. The biometry information associated with the first patient may include biometry information associated with an eye of the first patient.

At 720, second multiple locations associated with a face of a current patient may be determined. In one example, computer system 330 may determine second multiple locations associated with a face of a current patient. In a second example, microscope 350 may determine second multiple locations associated with a face of a current patient. In another example, MID 352 may determine second multiple locations associated with a face of a current patient.

The second multiple locations associated with the face of the current patient may be determined via at least one image acquired via an image sensor. For example, determining the second multiple locations associated with the face of the current patient may include determining the second multiple locations associated with the face of the current patient via at least one image from MID 352.

The current patient may be the first patient or may be another patient, which is not the first patient. In one example, the current patient may be patient 120. The second multiple locations associated with the face of the current patient may include locations 412A-412P. In another example, the current patient may be patient 420. The second multiple locations associated with the face of the current patient may include locations 410A-410P.

At 725, a second template of the face of the current patient based at least on the second multiple locations associated with the face of the current patient may be determined. In one example, computer system 330 may determine a second template of the face of the current patient based at least on the second multiple locations associated with the face of the current patient. In a second example, microscope 350 may determine a second template of the face of the current patient based at least on the second multiple locations associated with the face of the current patient. In another example, MID 352 may determine a second template of the face of the current patient based at least on the second multiple locations associated with the face of the current patient. The current patient may be the first patient or may be another patient, which is not the first patient. In one example, the current patient may be patient 120. The second template of the face of the current patient may be template 442. In another example, the current patient may be patient 420. The second template of the face of the current patient may be template 440.

At 730, it may be determined if the first template matches the second template. In one example, computer system 330 may determine if the first template matches the second template. In a second example, microscope 350 may determine if the first template matches the second template. In another example, MID 352 may determine if the first template matches the second template. Determining if the first template matches the second template may include determining if one or more locations of the first template match one or more locations of the second template. Determining if the first template matches the second template may include determining if a polygon formed by three or more locations of the first template matches a polygon formed by three or more locations of the second template.

If the first template does not match the second template, an indication the current patient has not been identified may be provided, at 735. In one example, computer system 330 may provide an indication the current patient has not been identified. In a second example, microscope 350 may provide an indication the current patient has not been identified. In another example, MID 352 may provide an indication the current patient has not been identified. Providing the indication that the current patient has not been identified includes providing at least one of a visual signal and an audible signal. Providing the indication that the current patient has not been identified may include a graphical user interface providing the indication that the current patient has not been identified. For example, GUI 415, illustrated in FIG. 4D, may provide the indication that the current patient has not been identified. Providing the indication that the current patient has not been identified may include providing an audible signal. For example, the audible signal may include one or more audible sounds.

If the first template matches the second template, an indication that the current patient has been correctly identified as the first patient may be provided, at 740. In one example, computer system 330 may provide an indication that the current patient has been correctly identified as the first patient. In a second example, microscope 350 may provide an indication that the current patient has been correctly identified as the first patient. In another example, MID 352 may provide an indication that the current patient has been correctly identified as the first patient. Providing the indication that the current patient has been correctly identified as the first patient may include a graphical user interface providing the indication that the current patient has been correctly identified as the first patient. For example, GUI 415, illustrated in FIG. 4E, may provide the indication that the current patient has been correctly identified as the first patient.

At 745, an angle of a microscope integrated display with respect to the face of the first patient may be determined based at least on the second template. In one example, computer system 330 may determine, based at least on the second template, an angle of a microscope integrated display with respect to the face of the first patient. In a second example, microscope 350 may determine, based at least on the second template, an angle of a microscope integrated display with respect to the face of the first patient. In another example, MID 352 may determine, based at least on the second template, an angle of a microscope integrated display with respect to the face of the first patient.

At 750, it may be determined, based at least on the second template, if surgical tooling equipment enters an area of the second template. In one example, computer system 330 may determine, based at least on the second template, if surgical tooling equipment enters an area of the second template. In a second example, microscope 350 may determine, based at least on the second template, if surgical tooling equipment enters an area of the second template. In a second example, microscope 350 may determine, based at least on the second template, if surgical tooling equipment enters an area of the second template. In another example, MID 352 may determine, based at least on the second template, if surgical tooling equipment enters an area of the second template.

Determining if surgical tooling equipment enters an area of the second template may include determining if surgical tooling equipment enters an incorrect area of the second template. For example, a surgery may be performed on eye 122 of patient 120 and may not be performed on eye 124. It may be determined if surgical tooling equipment 320 enters an area bounded by locations 412L-412P, as illustrated in FIG. 5C. For example, determining if surgical tooling equipment 320 enters the area bounded by locations 412L-412P may prevent a mistake.

If surgical tooling equipment enters an area of the second template, an indication that the surgical tooling equipment should not be in the area of the second template may be provided, at 755. In one example, computer system 330 may provide an indication that the surgical tooling equipment should not be in the area of the second template. In a second example, microscope 350 may provide an indication that the surgical tooling equipment should not be in the area of the second template. In another example, MID 352 may provide an indication that the surgical tooling equipment should not be in the area of the second template. Providing an indication that the surgical tooling equipment should not be in the area of the second template may be performed in response to determining, based at least on the second template, that surgical tooling equipment enters an area of the second template. Providing an indication that the surgical tooling equipment should not be in the area of the second template may include a graphical user interface providing an indication that the surgical tooling equipment should not be in the area of the second template. For example, GUI 510, illustrated in FIG. 5E, may provide an indication that the surgical tooling equipment should not be in the area (e.g., the area bounded by locations 412L-412P) of the second template. Providing an indication that the surgical tooling equipment should not be in the area of the second template may include providing an audible signal. For example, the audible signal may include one or more audible sounds. Providing the indication that the surgical tooling equipment should not be in the area of the second template may be performed in response to determining that the surgical tooling equipment enters the area of the second template.

If surgical tooling equipment does not enter an area of the second template, an indication of no errors may be provided, at 760. In one example, computer system 330 may provide an indication of no errors. In a second example, microscope 350 may provide an indication of no errors. In another example, MID 352 may provide an indication of no errors. A graphical user interface may provide an indication of no errors. A graphical user interface may provide an indication of no errors. For example, GUI 510, illustrated in FIG. 5F, may provide an indication of no errors.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A medical system, comprising:

at least one processor;

at least one display coupled to the processor; and a memory medium that is coupled to the at least one processor and that includes instructions, when executed by the at least one processor, cause the medical system to:

receive an identification of a first patient;

receive a first template that includes a first plurality of locations associated with a face of the first patient and associated with the identification of the first patient;

determine a second plurality of locations associated with a face of a current patient;

determine a second template of the face of the current patient based at least on the second plurality of locations associated with the face of the current patient;

determine if the first template matches the second template;

provide, via the at least one display, an indication related to whether the current patient has been correctly identified as the first patient;

determine, based at least on the second template, that surgical tooling equipment enters an area of the second template; and in response to determining, based at least on the second template, that the surgical tooling equipment enters the area of the second template, provide, via the at least one display, an indication that the surgical tooling equipment should not be in the area of the second template.

2. The medical system of claim 1, wherein, to provide the indication that the current patient has not been identified, the instructions further cause the medical system to provide at least one of a visual signal and an audible signal.

3. The medical system of claim 1, wherein the instructions further cause the medical system to:

determine the first plurality of locations associated with the face of the first patient;

determine the first template of the face of the first patient based at least on the first plurality of locations associated with the face of the first patient;

associate the first template with the identification of the first patient; and store the first template with the identification of the first patient.

4. The medical system of claim 1, wherein the instructions further cause the medical system to:

determine a third plurality of locations associated with a face of a second patient;

determine a third template of the face of the second patient based at least on the third plurality of locations associated with the face of the second patient;

associate the third template with an identification of the second patient; and store the third template with the identification of the second patient.

5. The medical system of claim 1, wherein the instructions further cause the medical system to determine an orientation of a lens with respect to the face of the first patient based at least on the second template.

6. A method, comprising:

a medical system receiving an identification of a first patient;

the medical system receiving a first template that includes a first plurality of locations associated with a face of the first patient and associated with the identification of the first patient;

the medical system determining a second plurality of locations associated with a face of a current patient;

the medical system determining a second template of the face of the current patient based at least on the second plurality of locations associated with the face of the current patient;

the medical system determining if the first template matches the second template;

providing, via a display of the medical system, an indication related to whether the current patient has been correctly identified as the first patient;

the medical system determining, based at least on the second template, that surgical tooling equipment enters an area of the second template; and in response to the determining, based at least on the second template, that the surgical tooling equipment enters the area of the second template, the medical system providing, via the display of the medical system, an indication that the surgical tooling equipment should not be in the area of the second template.

7. The method of claim 6, wherein the medical system providing the indication that the current patient has not been identified includes providing at least one of a visual signal and an audible signal.

8. The method of claim 6, further comprising:

the medical system determining the first plurality of locations associated with the face of the first patient;

the medical system determining the first template of the face of the first patient based at least on the first plurality of locations associated with the face of the first patient;

the medical system associating the first template with the identification of the first patient; and the medical system storing the first template with the identification of the first patient.

9. The method of claim 6, further comprising:

the medical system determining a third plurality of locations associated with a face of a second patient;

the medical system determining a third template of the face of the second patient based at least on the third plurality of locations associated with the face of the second patient;

the medical system associating the third template with an identification of the second patient; and the medical system storing the third template with the identification of the second patient.

10. The method of claim 6, further comprising:

the medical system determining an orientation of a lens with respect to the face of the first patient based at least on the second template.

* * * * *